United States Patent
Zhang et al.

(10) Patent No.: US 12,240,811 B2
(45) Date of Patent: Mar. 4, 2025

(54) N-HETEROCYCLIC FIVE-MEMBERED RING-CONTAINING CAPSID PROTEIN ASSEMBLY INHIBITOR, PHARMACEUTICAL COMPOSITION AND USES THEREOF

(71) Applicant: CHIA TAI TIANQING PHARMACEUTICAL GROUP CO., LTD., Lianyungang (CN)

(72) Inventors: Yinsheng Zhang, Lianyungang (CN); Wangwei Ao, Lianyungang (CN); Yuan Li, Lianyungang (CN); Hui Wang, Lianyungang (CN); Hangzhou Shen, Lianyungang (CN); Jie Ni, Lianyungang (CN); Huan Zhang, Lianyungang (CN); Jie Wu, Lianyungang (CN); Li Zhang, Lianyungang (CN); Kai Cao, Lianyungang (CN); Peng Lu, Lianyungang (CN); Xushi Liu, Lianyungang (CN); Jie Wang, Lianyungang (CN); Tianxiao Zhao, Lianyungang (CN); Xingfeng Ge, Lianyungang (CN); Dandan Lu, Lianyungang (CN); Shuo Chen, Lianyungang (CN); Xueqin Ma, Lianyungang (CN); Wei Shi, Lianyungang (CN); Xiaojin Wang, Lianyungang (CN); Hongjiang Xu, Lianyungang (CN)

(73) Assignee: CHIA TAI TIANQING PHARMACEUTICAL GROUP CO., LTD., Lianyungang (CN)

( * ) Notice: Subject to any disclaimer, the term of this patent is extended or adjusted under 35 U.S.C. 154(b) by 843 days.

(21) Appl. No.: 17/425,701

(22) PCT Filed: Sep. 27, 2019

(86) PCT No.: PCT/CN2019/108483
§ 371 (c)(1),
(2) Date: Jul. 23, 2021

(87) PCT Pub. No.: WO2020/151252
PCT Pub. Date: Jul. 30, 2020

(65) Prior Publication Data
US 2022/0185774 A1 Jun. 16, 2022

(30) Foreign Application Priority Data
Jan. 25, 2019 (CN) .......................... 201910073465.2

(51) Int. Cl.
C07D 207/34 (2006.01)
A61P 31/20 (2006.01)

(52) U.S. Cl.
CPC ............ *C07D 207/34* (2013.01); *A61P 31/20* (2018.01)

(58) Field of Classification Search
CPC ........ C07D 207/34; A61P 31/20; A61K 31/40
(Continued)

(56) References Cited

U.S. PATENT DOCUMENTS

| 11,597,716 B2* | 3/2023 | Zhang ................ C07D 405/12 |
| 2016/0176817 A1* | 6/2016 | Vandyck .............. C07D 401/12 546/208 |

(Continued)

FOREIGN PATENT DOCUMENTS

| CN | 101756890 | 6/2010 |
| CN | 102389400 | 3/2012 |

(Continued)

OTHER PUBLICATIONS

B. Testa, Biochemical Pharmacology 68 (2004) 2097-2106, "Prodrug research: futile or fertile?" (Year: 2004).*

(Continued)

*Primary Examiner* — Jared Barsky
*Assistant Examiner* — Liyuan Mou
(74) *Attorney, Agent, or Firm* — Fish & Richardson P.C.

(57) ABSTRACT

Provided is a compound of formula I or II, a stereoisomer, a tautomer, a geometrical isomer, a solvate, an active metabolite, a hydrate, a prodrug or a pharmaceutically acceptable salt thereof, a pharmaceutical composition thereof, and the medical uses thereof in treating diseases benefiting from the capsid protein assembly inhibitor, particularly diseases caused by hepatitis B virus infection.

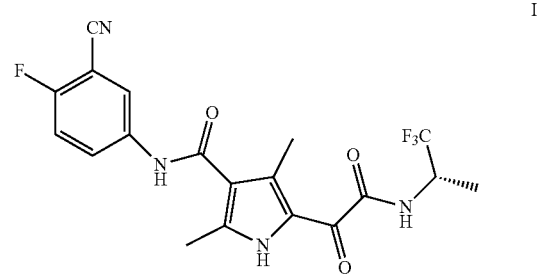

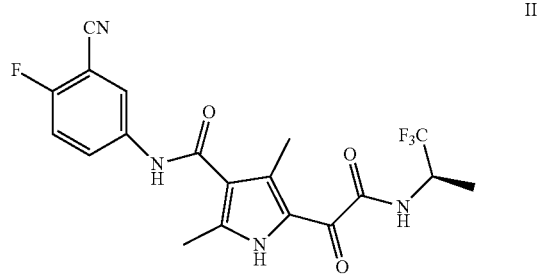

4 Claims, No Drawings

(58) Field of Classification Search
USPC .......................................................... 514/423
See application file for complete search history.

(56) References Cited

U.S. PATENT DOCUMENTS

| | | |
|---|---|---|
| 2021/0017154 A1 | 1/2021 | Zhang et al. |
| 2022/0185774 A1 | 6/2022 | Zhang et al. |
| 2022/0332684 A1 | 10/2022 | Wang et al. |
| 2022/0363634 A1 | 11/2022 | Lu et al. |

FOREIGN PATENT DOCUMENTS

| | | | |
|---|---|---|---|
| CN | 103705478 | | 4/2014 |
| CN | 105431413 A | | 3/2016 |
| CN | 105658624 A | | 6/2016 |
| CN | 105980378 | | 9/2016 |
| CN | 105431413 | | 1/2018 |
| CN | 105658624 | | 1/2019 |
| CN | 109153640 A | | 1/2019 |
| CN | 109790168 A | | 5/2019 |
| CN | 107721895 | | 3/2020 |
| RU | 2470916 | | 12/2012 |
| WO | WO 2006012642 A2 | | 2/2006 |
| WO | WO2014184350 | | 11/2014 |
| WO | WO2015011281 | | 1/2015 |
| WO | WO2017156255 | | 9/2017 |
| WO | WO-2017156255 A1 * | 9/2017 | .............. A61K 31/40 |
| WO | WO2018039531 | | 3/2018 |
| WO | WO2018050110 | | 3/2018 |
| WO | WO2019165374 | | 8/2019 |
| WO | WO 2019165374 A1 | | 8/2019 |
| WO | WO2019185016 | | 10/2019 |
| WO | WO 2019185016 A1 | | 10/2019 |
| WO | WO2019241292 | | 12/2019 |
| WO | WO-2019241292 A1 * | 12/2019 | .............. A61P 31/20 |
| WO | WO 2020151252 A1 | | 7/2020 |
| WO | WO 2020156494 | | 8/2020 |
| WO | WO 2021058002 | | 4/2021 |
| WO | WO 2021119081 | | 6/2021 |

OTHER PUBLICATIONS

Nijampatnam et al. Current Opinion in Chemical Biology 2019, 50:73-79, Recent advances in the development of HBV capsid assembly modulators (Year: 2019).*
JP Office Action in Japanese Appln. No. 2021-542370, dated Oct. 3, 2023, 9 pages (with English translation).
Nozaki et al., "Medicinal Drug Chemistry (Soyaku Kagaku)," 1st ed., Jul. 1, 1995, Chapter 5.2.2, pp. 98-99 (with English abstract).
CN Office Action in Chinese Appln. No. 202080066483.9, dated Oct. 13, 2023, 10 pages (with English translation).
He et al., "Hepatitis B virus replication mechanisms and drug targets of chronic hepatitis B," Chinese Pharmacological Bulletin, Feb. 2015, 31(2):152-156 (with English abstract).
Alekseyev, V.V., "Optical Isomerism and Drugs Pharmacological Activity," Soros Educational Journal, 1998, pp. 49-55 (8 pages).
International Search Report and Written Opinion in International Appln. No. PCT/CN2019/108483, dated Jan. 2, 2020, 28 pages.
International Search Report and Written Opinion in PCT/CN2020/118426, mailed on Jan. 5, 2021, 22 pages.
Knunyants, I.L., "Chemical Encyclopedic Dictionary," Moscow, Soviet Encyclopedia, 1983, pp. 130-131.
Kummerer, Klaus, "Pharmaceuticals in the Environment," Annu. Rev. Environ. Resourc., 2010, 35:57-75.
RU Office Action in Russian Appln. No. 2021123614/04, dated Feb. 28, 2023, 27 pages (with English translation).
International Preliminary Report on Patentability in International Appln. No. PCT/CN2020/118426, dated Mar. 15, 2022, 13 pages (with English translation).
Brahmania, et al., "New therapeutic agents for chronic hepatitis B," The Lancet Infectious Diseases, Jan. 13, 2016, 16(2):e10-e21.
Greene's Protective Groups in Organic Synthesis (4th Ed). Hoboken, New Jersey: John Wiley & Sons, Inc., chapter 2.
Greene's Protective Groups in Organic Synthesis, 4th ed., Wuts and Greene (eds)., Apr. 2006, Chapter 2, 351 pages.
Office Action in Eurasian Appln. No. 202092159, dated Sep. 17, 2021, 7 pages (with English translation).
Extended European Search Report in European Appln. No. 19777163.7, dated Nov. 25, 2021, 7 pages.
International Preliminary Report on Patentability in International Appln. No. PCT/CN2019/108483, dated Aug. 5, 2021, 17 pages (with English translation).

* cited by examiner

N-HETEROCYCLIC FIVE-MEMBERED RING-CONTAINING CAPSID PROTEIN ASSEMBLY INHIBITOR, PHARMACEUTICAL COMPOSITION AND USES THEREOF

PRIORITY CLAIM

The present application is a U.S. National Phase application under 35 U.S.C. § 371 of International Patent Application No. PCT/CN2019/108483, filed on Sep. 27, 2019, which claims priority to Chinese patent application No. CN201910073465.2, filed on Jan. 25, 2019, the disclosure of each of which is incorporated herein by reference in its entirety.

TECHNICAL FIELD

The present application relates to a compound of Formula I or II, a stereoisomer, a tautomer, a geometric isomer, a solvate, an active metabolite, a hydrate, a prodrug or a pharmaceutically acceptable salt thereof, and a process for the preparation thereof, a pharmaceutical composition comprising the same, and use thereof for preventing or treating a disease (such as a disease that benefits from the inhibition of capsid protein assembly, for example, as a drug for treating hepatitis B virus infection.

BACKGROUND

Currently, chronic hepatitis B cannot be cured and only controlled, and is limited to two types of drugs (interferons and nucleoside analogs/inhibitors of viral polymerases). The lower cure rate of HBV is partially due to the presence and persistence of covalently closed circular DNA (cccDNA) in the nucleus of infected hepatocytes. Current treatment protocols are unable to remove cccDNA from the repository, and some new targets for HBV such as Core inhibitors (such as viral capsid protein formation or assembly inhibitors, cccDNA inhibitors, interferon-stimulated gene activators, and etc.) is expected to bring hope to curing hepatitis B (Mayur Brahmania, et al. New therapeutic agents for chronic hepatitis B).

The HBV capsid is assembled from the core protein. HBV reverse transcriptase and pgRNA need to be correctly encapsulated before reverse transcription. Therefore, blocking capsid protein assembly, or accelerating capsid protein degradation would block the assembly process of the capsid protein, and thereby affecting viral replication. In recent years, researchers have begun to study inhibitors targeting capsid protein assembly, for example, WO2014184350, WO2015011281, WO2017156255, etc., disclose a series of related compounds. However, most of them are in the early stage of clinical research or the research has been terminated, and there is a need in the art for more alternative effective capsid protein assembly inhibitors for treating, ameliorating or preventing HBV infection.

DETAILED DESCRIPTION OF THE INVENTION

The present application relates to a compound of Formula I, a stereoisomer, a tautomer, a geometric isomer, a solvate, an active metabolite, a hydrate, a prodrug or a pharmaceutically acceptable salt thereof,

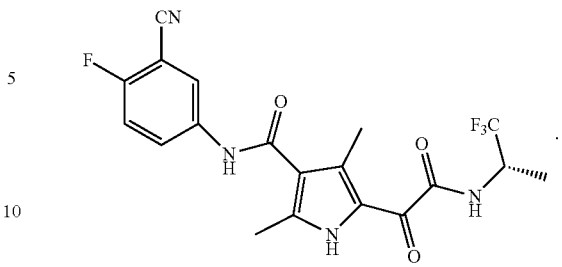

The present application also relates to a compound of Formula II, a stereoisomer, a tautomer, a geometric isomer, a solvate, an active metabolite, a hydrate, a prodrug or a pharmaceutically acceptable salt thereof,

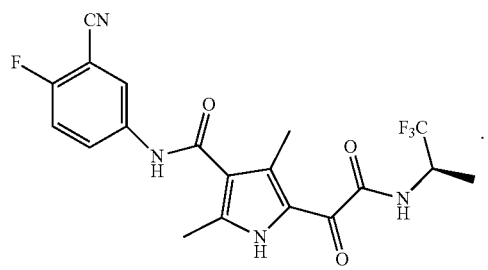

In another aspect, the application provides a pharmaceutical composition comprising a compound of Formula I or II, or a pharmaceutically acceptable salt thereof of the present application. In some embodiments, the pharmaceutical composition of the present application further comprises a pharmaceutically acceptable excipient.

In another aspect, the present application provides a method for treating a disease that benefits from the inhibition of capsid protein assembly, comprising administering to a mammal, preferably a human, in need of such treatment a therapeutically effective amount of a compound of the above Formula I or II, a pharmaceutically acceptable salt thereof or a pharmaceutical composition thereof.

In another aspect, the present application also provides use of a compound of the above Formula I or II, a pharmaceutically acceptable salt thereof, or a pharmaceutical composition thereof, in the preparation of a medicament for preventing or treating a disease that benefits from the inhibition of capsid protein assembly.

In another aspect, the present application provides use of a compound of the above Formula I or II, a pharmaceutically acceptable salt thereof, or a pharmaceutical composition thereof, for preventing or treating a disease that benefits from the inhibition of capsid protein assembly.

In another aspect, the present application provides a compound of the above Formula I or II, a pharmaceutically acceptable salt thereof, or a pharmaceutical composition thereof, for use in preventing or treating a disease that benefits from the inhibition of capsid protein assembly.

In another aspect, the application provides a pharmaceutical composition comprising a compound of Formula I or II, a stereoisomer, a tautomer, a geometric isomer, a solvate, an active metabolite, a hydrate, a prodrug or a pharmaceutically acceptable salt thereof of the present application. In some embodiments, the pharmaceutical composition of the present application further comprises a pharmaceutically acceptable excipient.

In another aspect, the present application provides a method for inhibiting capsid protein assembly comprising administering to a subject in need thereof a therapeutically effective amount of a compound of Formula I or II, a stereoisomer, a tautomer, a geometric isomer, a solvate, an active metabolite, a hydrate, a prodrug, a pharmaceutically acceptable salt thereof or pharmaceutical composition thereof of the present application. In some embodiments, said subject is a mammal; in some embodiments, said subject is a human.

In another aspect, the present application provides a method for preventing or treating a disease that benefits from the inhibition of capsid protein assembly, comprising administering to a subject in need thereof a therapeutically effective amount of a compound of Formula I or II, a stereoisomer, a tautomer, a geometric isomer, a solvate, an active metabolite, a hydrate, a prodrug, a pharmaceutically acceptable salt thereof, or a pharmaceutical composition thereof of the present application. In some embodiments, said subject is a mammal; in some embodiments, said subject is a human.

In another aspect, the present application provides use of a compound of Formula I or II, a stereoisomer, a tautomer, a geometric isomer, a solvate, an active metabolite, a hydrate, a prodrug or a pharmaceutically acceptable salt thereof, or a pharmaceutical composition thereof of the present application for inhibiting capsid protein assembly.

In another aspect, the present application also provides use of a compound of the Formula I or II, a stereoisomer, a tautomer, a geometric isomer, a solvate, an active metabolite, a hydrate, a prodrug, a pharmaceutically acceptable salt thereof, or a pharmaceutical composition thereof of the present application in the preparation of a medicament for inhibiting capsid protein assembly.

In another aspect, the present application also provides use of a compound of the Formula I or II, a stereoisomer, a tautomer, a geometric isomer, a solvate, an active metabolite, a hydrate, a prodrug, a pharmaceutically acceptable salt thereof, or a pharmaceutical composition thereof of the present application in the preparation of a medicament for preventing or treating a disease that benefits from the inhibition of capsid protein assembly.

In another aspect, the present application also provides use of a compound of the above Formula I or II, a stereoisomer, a tautomer, a geometric isomer, a solvate, an active metabolite, a hydrate, a prodrug or a pharmaceutically acceptable salt thereof, or a pharmaceutical composition thereof for preventing or treating a disease that benefits from the inhibition of capsid protein assembly.

In another aspect, the present application provides a compound of Formula I or II, a stereoisomer, a tautomer, a geometric isomer, a solvate, an active metabolite, a hydrate, a prodrug or a pharmaceutically acceptable salt thereof, or a pharmaceutical composition thereof of the present application for use in inhibiting capsid protein assembly.

In another aspect, the present application provides a compound of the above Formula I or II, a stereoisomer, a tautomer, a geometric isomer, a solvate, an active metabolite, a hydrate, a prodrug, a pharmaceutically acceptable salt thereof, or a pharmaceutical composition thereof for use in preventing or treating a disease that benefits from the inhibition of capsid protein assembly.

In some embodiments of the present application, the disease that benefits from the inhibition of capsid protein assembly is a disease caused by hepatitis B virus (HBV) infection.

In some embodiments of the present application, the disease that benefits from inhibition of capsid protein assembly is a liver disease caused by hepatitis B virus (HBV) infection.

In some embodiments of the present application, the treating disease that benefits from inhibition of capsid protein assembly is to control, reduce or eliminate HBV to prevent, alleviate or cure liver disease in an infected patient.

Definition

Unless stated otherwise, the terms and phrases used herein have the following meanings. A specific term or phrase shall not be considered as indefinite or unclear when it is not specifically defined, but should be understood according to the general meaning thereof. The trade names used herein refer to the corresponding products or the active ingredients thereof.

Term "optional" or "optionally" means that the subsequently described event or situation may or may not occur, and the description includes instances in which the event or situation occurs and instances in which the event or situation does not occur. For example, an ethyl group "optionally" substituted with halo means that the ethyl group may be unsubstituted ($CH_2CH_3$), monosubstituted (e.g., $CH_2CH_2F$), polysubstituted (e.g. $CHFCH_2F$, $CH_2CHF_2$, etc.) or completely substituted ($CF_2CF_3$). It will be understood by a person skilled in the art that for any group containing one or more substituents, no substitution or substitution pattern that is sterically impossible to exist and/or which cannot be synthesized is introduced.

The term "treating" or "treatment" refers to the administration of a compound or formulation described in the present application to ameliorate or eliminate a disease or one or more symptoms associated with the disease, and comprises:

(i) inhibiting the disease or disease condition, i.e., curbing its development;
(ii) alleviating the disease or disease condition, i.e., regressing the disease or disease condition.

The term "preventing" means administering the compound or formulation of the present application to prevent a disease or one or more symptoms associated with the disease, and includes: preventing the occurrence of the disease or disease state in a mammal, particularly when such a mammal is predisposed to the disease state but has not yet been diagnosed as having it.

The term "therapeutically effective amount" means an amount of a compound of the present application for (i) treating or preventing a particular disease, condition or disorder, (ii) alleviating, ameliorating or eliminating one or more symptoms of a particular disease, condition or disorder, or (iii) preventing or delaying the onset of one or more symptoms of disease, condition or disorder described herein. The "therapeutically effective amount" of a compound of this application varies depending on the compound, the disease condition and its severity, the mode of administration, and the age of the mammal to be treated, but can be routinely determined by those skilled in the art according to their own knowledge and the present disclosure.

The term "pharmaceutically acceptable" refers to those compounds, materials, compositions and/or dosage forms that are within the scope of sound medical judgment and are suitable for use in contact with human and animal tissues without excessive toxicity, irritation, allergic reactions or other problems or complications, and are commensurate with a reasonable benefit/risk ratio.

As a pharmaceutically acceptable salt, for example, a metal salt, an ammonium salt, a salt formed with an organic base, a salt formed with an inorganic acid, a salt formed with an organic acid, a salt formed with a basic or acidic amino acid, or the like can be mentioned.

The term "pharmaceutical composition" refers to a mixture of one or more compounds of the present application or a salt thereof and a pharmaceutically acceptable excipient. The purpose of the pharmaceutical composition is to facilitate the administration of the compounds of the present application to a subject.

The term "solvate" refers to a substance formed by combining a compound of the present application with a pharmaceutically acceptable solvent. Pharmaceutically acceptable solvents include water, ethanol, acetic acid, and the like. Solvates include stoichiometric solvates and non-stoichiometric solvates.

The term "hydrate" refers to a solvate comprising a compound disclosed or claimed and a stoichiometric or non-stoichiometric amount of water.

The compounds of the present application may also be prepared as prodrugs, such as pharmaceutically acceptable prodrugs. Since prodrugs are known to improve many desired properties of a drug (e.g., solubility, bioavailability, preparation, etc.), the compounds of the present application can be delivered in the form of a prodrug. Accordingly, the present application is intended to encompass prodrugs of currently claimed compounds, methods of delivery thereof, and compositions containing prodrugs.

The term "prodrug" is intended to include any covalently bonded carrier which, when administered to a mammalian subject, releases the active parent drug of the present application in vivo. The prodrugs of the present application are prepared by modifying a functional group present in the compound in such a manner that the modification cleaves into the parent compound in a conventional operation or in vivo.

In the present application, the term "subject" includes humans and animals, for example, mammals (e.g., primates, cows, horses, pigs, dogs, cats, mice, rats, rabbits, goats, sheeps, birds, etc.).

The term "active metabolite" refers to a biologically active derivative of a compound that is formed when the compound is metabolized.

The term "pharmaceutically acceptable excipient" refers to those excipients which have no significant irritating effect on the organism and do not impair the biological activity and properties of the active compound. Suitable excipients are well known to those skilled in the art, such as carbohydrates, waxes, water soluble and/or water swellable polymers, hydrophilic or hydrophobic materials, gelatin, oils, solvents, water, and the like.

The word "comprise" and its English variants such as "comprises" or "comprising" shall be understood in an open, non-exclusive sense, i.e., "including, but not limited to".

The compounds and intermediates of the present application may also exist in different tautomeric forms, and all such forms are encompassed within the scope of the present application. The term "tautomer" or "tautomeric form" refers to structural isomers with different energies that are interconvertible via a low energy barrier. For example, proton tautomers (also known as proton transfer tautomers) include interconversions via proton transfer, such as keto-enol and imine-enamine isomerization. A specific example of a proton tautomer is an imidazole moiety in which a proton can migrate between two ring nitrogen atoms. Valence tautomers include recombination tautomers through some of the bond-forming electrons.

Certain compounds of the present application may have asymmetric carbon atoms (stereocenters) or double bonds. Thus, racemates, diastereomers, enantiomers, geometric isomers, and individual isomers are included within the scope of the present application.

Unless otherwise specified, when the compounds of the present application contain olefinic double bonds or other centers of geometric asymmetry, they include the E and Z geometric isomers.

The compounds of the present application may exist in specific geometric or stereoisomeric forms. The present application contemplates all such compounds, including tautomers, cis and trans isomers, (−)- and (+)-enantiomers, (R)- and (S)-enantiomers, diastereoisomers, (D)-isomers, (L)-isomers, and racemic mixtures thereof, and other mixtures, such as enantiomers- or diastereomers-enriched mixtures, all of which fall within the scope of the present application. Additional asymmetric carbon atoms may be present in the substituents such as alkyl, etc. All these isomers and their mixtures are included within the scope of the present application.

The optically active (R)- and (S)-isomers as well as the D and L isomers can be prepared by chiral synthesis or chiral reagents or other conventional techniques. An enantiomer of a certain compound of the present application can be prepared by asymmetric synthesis or by derivatization with a chiral auxiliary, wherein the resulting diastereomeric mixture is separated and the auxiliary group is cleaved to provide the pure desired enantiomers. Alternatively, when a molecule contains a basic functional group (such as amino) or an acidic functional group (such as carboxyl), it forms a salt of diastereomer with a suitable optically active acid or base, and then a diastereomer resolution is performed by a conventional method well known in the art, then the pure enantiomer is recovered. In addition, the separation of the enantiomers and diastereomers is generally accomplished by using chromatography with a chiral stationary phase, and optionally in combination with chemical derivatization method (e.g., formation of carbamates from amines).

The present application also includes isotopically labeled compounds of the present application that are identical to those described herein, but in which one or more atoms are replaced by those having an atomic weight or mass number different from the atomic mass or mass number normally found in nature. Examples of isotopes that may be incorporated into the compounds of the present application include isotopes of hydrogen, carbon, nitrogen, oxygen, phosphorus, sulfur, fluorine, iodine, and chlorine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{123}I$, $^{125}I$, $^{36}Cl$ and the like, respectively.

Certain isotopically-labeled compounds of the present application (such as those labeled with $^{3}H$ and $^{14}C$) can be used in compound and/or substrate tissue distribution assays. Deuterated (i.e., $^{3}H$) and carbon-14 (i.e., $^{14}C$) isotopes are especially preferred for their ease of preparation and detectability. Positron emitting isotopes such as $^{15}O$, $^{13}N$, $^{11}C$, and $^{18}F$ can be used in positron emission tomography (PET) studies to determine substrate occupancy. Isotopically labeled compounds of the present application can generally be prepared by replacing a non-isotopically labeled reagent with an isotopically labeled reagent through procedures similar to those disclosed in the schemes and/or examples disclosed below.

Furthermore, substitution with heavier isotopes such as deuterium (i.e., $^2$H) may provide certain therapeutic advantages resulting from higher metabolic stability (e.g, increased in vivo half-life or reduced dosage requirements), and thus may be preferred in some cases, wherein the deuterium substitution may be partial or complete, and the partial deuterium substitution means that at least one hydrogen is substituted with at least one deuterium, and all such forms of the compounds are encompassed within the scope of the present application.

The pharmaceutical composition of the present application can be prepared by combining a compound of the present application with a suitable pharmaceutically acceptable excipient, and may be formulated into, for example, solid, semi-solid, liquid or gaseous formulations, such as tablets, pills, capsules, powders, granules, pastes, emulsions, suspensions, suppositories, injections, inhalants, gels, microspheres, aerosols and the like.

Typical administration routes of the compound of the present application or a pharmaceutically acceptable salt thereof, or a pharmaceutical composition comprising the same, include, but are not limited to, oral, rectal, topical, inhaled, parenteral, sublingual, intravaginal, intranasal, intraocular, intraperitoneal, intramuscular, subcutaneous, or intravenous administration.

The pharmaceutical composition of the present application can be manufactured through the well-known methods in the art, such as a conventional mixing method, dissolving method, granulation method, sugar-coated-pill method, grinding method, emulsification method, and freeze-drying method, etc.

In some embodiments, the pharmaceutical composition is in an oral administration form. For oral administration, the active compound can be mixed with the pharmaceutically acceptable carriers well-known in the art, to prepare the pharmaceutical composition. With these excipients, the compounds of the present application can be formulated into tablets, pills, lozenges, dragees, capsules, liquid, gels, syrup, or suspensions and the like, for oral administration to patients.

The solid oral composition can be prepared by conventional mixing, filling or tabletting method. For example, it can be obtained through the following method: mixing the active compound with a solid excipient; optionally grinding the resulting mixture, adding other suitable excipients if needed; and then processing the mixture into granules to obtain the core of tablets or dragees. Suitable excipients include, but are not limited to, adhesives, diluents, disintegrants, lubricants, glidants, sweeteners and/or flavoring agents, etc.

The pharmaceutical composition is also suitable for parenteral administration, such as sterile solutions, suspensions or freeze-dried products in an appropriate unit dose form.

The therapeutic dosage of the compounds of the present application can be determined according to, for example, the particular use of the treatment, the administration route of the compound, the health and condition of the patient, and the judgment of the prescribing physician. The proportion or concentration of the compounds of the present application in a pharmaceutical composition may vary depending on a variety of factors including dosage, chemical characteristics (e.g., hydrophobicity) and the route of administration. For example, the compound of the present application can be provided in a physiologically buffered aqueous solution containing about 0.1 to 10% w/v of the compound for parenteral administration. Some typical doses range from about 1 lag/kg to about 1 g/kg body weight per day. In certain embodiments, the dose range is from about 0.01 mg/kg to about 100 mg/kg body weight per day. The dosage is likely to depend on such variables as the type and progression extent of the disease or condition, the general health state of the particular patient, the relative biological efficacy of the selected compound, the formulation of the excipient, and the route of administration thereof. An effective dose can be obtained by extrapolation from a dose-response curve derived from an in vitro or animal model test system.

The compounds of the present application can be prepared through a variety of synthetic processes well-known to those skilled in the art, including the specific embodiments listed below, embodiments formed by combining the specific embodiments with other chemical synthetic processes, and equivalent alternatives known to a person skilled in the art. Preferred embodiments include, but are not limited to, the working examples of the present application.

The chemical reaction of a specific embodiment of the present application is carried out in a suitable solvent, which should be suitable for the chemical changes of the present application and the required reagents and materials in the present application. In order to obtain the compounds of the present application, a person skilled in the art sometimes needs to modify or select a synthesis step or a reaction process on the basis of the existing embodiments.

An important consideration in the design of synthetic routes in the art is the selection of a suitable protecting group for a reactive functional group (such as an amino group in this application), for example, reference may be made to Greene's Protective Groups in Organic Synthesis (4th Ed). Hoboken, New Jersey: John Wiley & Sons, Inc. All references cited in the present application are incorporated herein in their entireties.

The present application employs the following abbreviations:

EA represents ethyl acetate; MeOH represents methanol; DMF represents N,N-dimethylformamide; HATU represents O-(7-azabenzotriazol-1-yl)-N,N,N',N'-tetramethyluronium hexafluorophosphate; DIPEA represents N,N-diisopropylethylamine; PO represents oral administration; IV represents intravenous injection; DMSO represents dimethyl sulfoxide.

For clarity, the present application is further illustrated by the following examples, but the examples are not intended to limit the scope of the present application. All reagents used in this application are commercially available and can be used without further purification.

EXAMPLES

The nuclear magnetic resonance (NMR) of the present application was detected by BRUKER-300 and BRUKER-500 nuclear magnetic resonance spectrometer, and tetramethylsilane (TMS=S 0.00) was employed as an internal standard of the chemical shift, and the nuclear magnetic resonance data was recorded as: proton number, peak type (s, singlet; d, doublet; t, triplet; q, quartet; m, multiplet), coupling constant (in Hz). AB SCIEX Triple TOF 4600 or AB SCIEX 3200QTRAP was employed as mass spectrometry instrument.

Example 1 (S)—N-(3-cyano-4-fluorophenyl)-2,4-dimethyl-5-(2-oxo-2-((1,1,1-trifluoroprop-2-yl)amino)acetyl)-1H-pyrrole-3-carboxamide

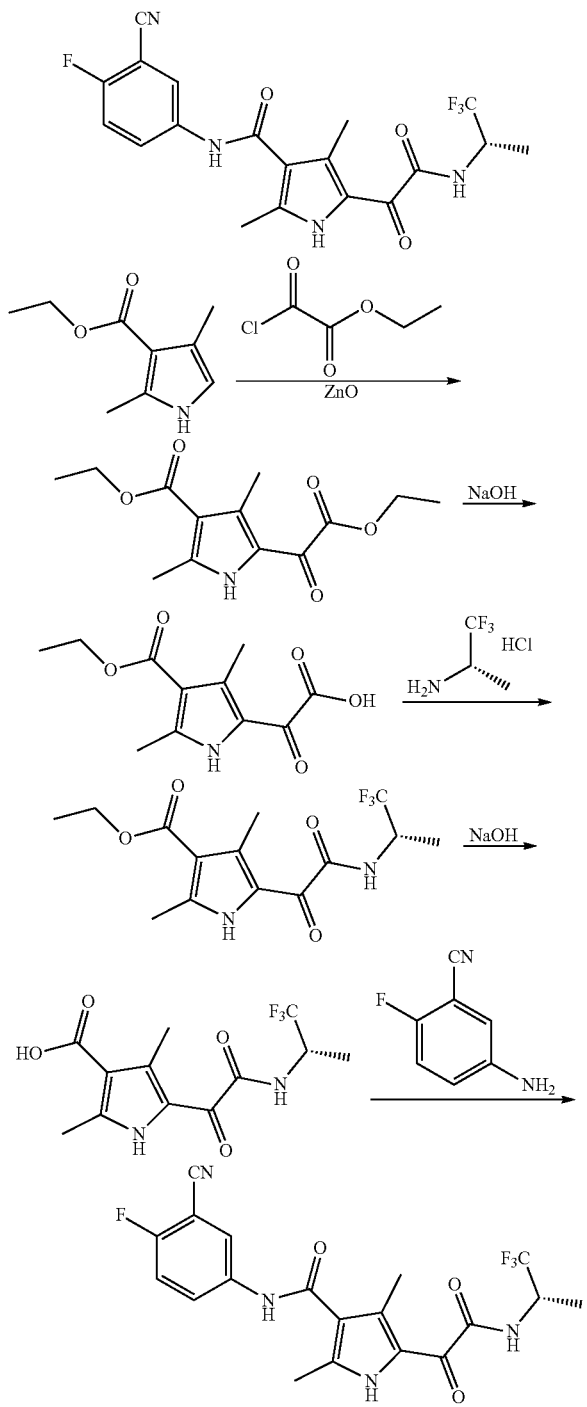

Step A: Ethyl 2-chloro-2-oxoacetate (40.8 g) and zinc oxide (1.22 g) were added sequentially into a reaction flask in an ice bath under N₂ protection, followed by adding ethyl 2,4-dimethyl-1H-pyrrole-3-carboxylate (5 g). After the addition, the mixture was stirred for 10 minutes in an ice bath, and then stirred at room temperature after removing the ice bath. After the reaction was finished, the reaction solution was slowly added dropwise into a 200 mL ice-water mixture, followed by adding EA (200 mL). The resulting mixture was layered. The organic phase was dried over anhydrous sodium sulfate, concentrated, and subjected to column chromatography to give ethyl 5-(2-ethoxy-2-oxoacetyl)-2,4-dimethyl-1H-pyrrole-3-carboxylate (4.5 g). MS (ESI+, [M+Na]⁺) m/z: 290.07.

Step B: ethyl 5-(2-ethoxy-2-oxoacetyl)-2,4-dimethyl-1H-pyrrole-3-carboxylate (3.5 g), and MeOH (40 mL) were added sequentially into a reaction flask. Then a solution of sodium hydroxide (1.05 g) in water (20 mL) was added dropwise under an ice bath, and the mixture was stirred at room temperature. After the reaction was finished, the aqueous phase was adjusted to pH 3-4 with a 2N hydrochloric acid aqueous solution, and then extracted with EA (100 mL*2). The organic phase was washed with water (30 mL) and concentrated to give 2-(4-(ethoxycarbonyl)-3,5-dimethyl-1H-pyrrol-2-yl)-2-oxoacetic acid (2.7 g). MS (ESI−, [M-H]⁻) m/z: 238.1.

Step C: 2-(4-(ethoxycarbonyl)-3,5-dimethyl-1H-pyrrol-2-yl)-2-oxoacetic acid (1 g), DMF (20 mL), HATU (2.07 g) and DIPEA (1.08 g) were sequentially added into a reaction flask at room temperature. After the addition, the reaction solution was stirred at room temperature for 10 minutes, followed by adding (S)-1,1,1-trifluoropropan-2-amine hydrochloride (0.63 g). After the reaction was finished, the reaction solution was poured into 50 mL water, and then extracted with EA (50 mL*3). The organic phase was washed with a saturated sodium sulfate aqueous solution (50 mL*3), dried over anhydrous sodium sulfate, and then filtered. The filtrate was collected, concentrated, and then purified by column chromatography to give ethyl (S)-2,4-dimethyl-5-(2-oxo-2-((1,1,1-trifluoroprop-2-yl)amino)acetyl)-1H-pyrrole-3-carboxylate (0.5 g). MS (ESI−, [M-H]⁻) m/z: 333.4.

Step D: ethyl (S)-2,4-dimethyl-5-(2-oxo-2-((1,1,1-trifluoroprop-2-yl)amino)acetyl)-1H-pyrrole-3-carboxylate (300 mg), and MeOH (2 mL) were added into a reaction flask, followed by adding a solution of NaOH (72 mg) in water (1 mL). After the addition, the reaction solution was heated to 80° C. and reacted overnight. After the reaction was finished, the resulting mixture was concentrated, and then thereto were added water (20 mL) and EA (60 mL) were added. The aqueous layer was separated. The organic phase was washed with water (30 mL) and layered. The aqueous phases were combined, adjusted to pH about 3 with 2N hydrochloric acid, extracted by adding EA (100 mL*2) and then layered. The organic phase was concentrated to give (S)-2,4-dimethyl-5-(2-oxo-2-((1,1,1-trifluoroprop-2-yl)amino)acetyl)-1H-pyrrole-3-carboxylic acid (230 mg). MS (ESI−, [M-H]⁻) m/z: 305.4.

Step E: (S)-2,4-dimethyl-5-(2-oxo-2-((1,1,1-trifluoroprop-2-yl)amino)acetyl)-1H-pyrrole-3-carboxylic acid (230 mg), DMF (5 mL), HATU (428 mg) and DIPEA (194 mg) were added sequentially into a reaction flask at room temperature. After the addition, the reaction solution was stirred for 10 minutes, followed by adding 5-amino-2-fluorobenzonitrile (123 mg). The resulting mixture was heated to 40° C. and stirred to react for 20 hours. After the reaction was finished, water (20 mL) and EA (60 mL) were added, and the mixture was layered. The organic layer was dried over anhydrous sodium sulfate, and then filtered. The filtrate was collected, rotary-evaporated to dryness, sampled and purified by column chromatography to give (S)—N-(3-cyano-4-fluorophenyl)-2,4-dimethyl-5-(2-oxo-2-((1,1,1-trifluoroprop-2-yl)amino)acetyl)-1H-pyrrole-3-carboxamide (180 mg). ¹H NMR (500 MHz, DMSO-d6) δ 12.05 (s, 1H), 10.20

(s, 1H), 9.49 (d, J=9.0 Hz, 1H), 8.20 (dd, J=6.0, 2.5 Hz, 1H), 7.98-7.91 (m, 1H), 7.53 (t, J=9.0 Hz, 1H), 4.78-4.67 (m, 1H), 2.40 (s, 3H), 2.32 (s, 3H), 1.34 (d, J=7.0 Hz, 3H). MS (ESI–, [M-H]⁻) m/z: 423.0.

Example 2 (R)—N-(3-cyano-4-fluorophenyl)-2,4-dimethyl-5-(2-oxo-2-((1,1,1-trifluoroprop-2-yl)amino)acetyl)-1H-pyrrole-3-carboxamide

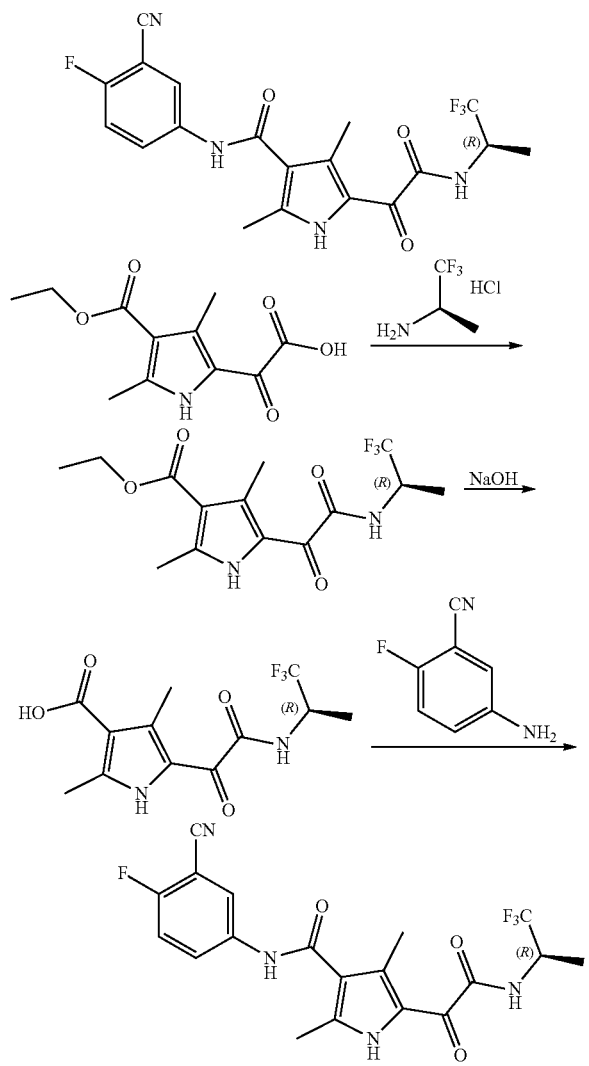

Step A: according to Example 1, (S)-1,1,1-trifluoropropan-2-amine hydrochloride was replaced with (R)-1,1,1-trifluoropropan-2-amine hydrochloride in step C to give ethyl (R)-2,4-dimethyl-5-(2-oxo-2-((1,1,1-trifluoroprop-2-yl)amino)acetyl)-1H-pyrrole-3-carboxylate. MS (ESI–, [M-H]⁻) m/z: 333.2.

Step B: according to Example 1, ethyl (S)-2,4-dimethyl-5-(2-oxo-2-((1,1,1-trifluoroprop-2-yl)amino)acetyl)-1H-pyrrole-3-carboxylate was replaced with ethyl (R)-2,4-dimethyl-5-(2-oxo-2-((1,1,1-trifluoroprop-2-yl)amino)acetyl)-1H-pyrrole-3-carboxylate in step D to give (R)-2,4-dimethyl-5-(2-oxo-2-((1,1,1-trifluoroprop-2-yl)amino)acetyl)-1H-pyrrole-3-carboxylic acid. MS (ESI–, [M-H]⁻) m/z: 305.4.

Step C: according to Example 1, (S)-2,4-dimethyl-5-(2-oxo-2-((1,1,1-trifluoroprop-2-yl)amino)acetyl)-1H-pyrrole-3-carboxylic acid was replaced with (R)-2,4-dimethyl-5-(2-oxo-2-((1,1,1-trifluoroprop-2-yl)amino)acetyl)-1H-pyrrole-3-carboxylic acid in step E to give (R)—N-(3-cyano-4-fluorophenyl)-2,4-dimethyl-5-(2-oxo-2-((1,1,1-trifluoroprop-2-yl)amino)acetyl)-1H-pyrrole-3-carboxamide. ¹H-NMR (500 MHz, DMSO-d6): δ 12.03 (s, 1H), 10.19 (s, 1H), 9.48 (d, J=8.5 Hz, 1H), 8.20 (dd, J=6.0, 2.5 Hz, 1H), 8.00-7.90 (m, 1H), 7.52 (t, J=9.0 Hz, 1H), 4.90-4.65 (m, 1H), 2.40 (s, 3H), 2.33 (s, 3H), 1.34 (d, J=7.5 Hz, 3H). MS (ESI–, [M-H]⁻) m/z: 423.2.

Experimental Example 1: In Vitro Activity Study 1.1 In Vitro Cell HBV DNA Inhibitory Activity A bottle of HepG2.2.15 (Wuhan Institute of Virology) or HepAD38 cells in good exponential growth state was taken, washed once by adding 5 mL PBS, and then thereto was added 3 mL trypsin. After digesting at room temperature for 5 min, 2 mL trypsin was discarded, and then the sample was placed in a cell culture incubator and digested for 10 min. The cells were taken out and observed under a microscope (whether the cells were individually round and there was no adhesion between the cells). 10 mL complete medium was added to terminate the digestion. After pipetting into a single cell suspension, 10 μL of the cell suspension was taken out for cell counting with a cell counter, and then diluted with a complete medium and adjusted to a cell density of $1*10^5$ cells/mL. Then the cell suspension was seeded at 1 mL/well in a 24-well plate with a multi-channel pipette (the 24-well plate was coated with 50 μg/mL Collagen I solution in advance), and cultured in a constant temperature $CO_2$ incubator for 48 h.

Compounds dissolved in DMSO were subjected to two-fold gradient dilution (10 concentrations in total) with complete medium. The compound was added, and fresh medium containing the compound was used to replace the spent medium every 72 hours. The cells were treated with the compound for 6 days. After the supernatant was siphoned off, 300 μL lysate (10 mM Tris-HCl, 1 mM EDTA, and 1% NP-40) was added to each well. After lysing at room temperature for 10 min, DNA was extracted, and HBV DNA in the intracellular viral capsid was measured by real-time fluorescence quantitative PCR. The inhibition rate was calculated based on the Ct value, and the EC50 value was calculated by the four-parameter method. The results are shown in Tables 1 and 2.

TABLE 1

Experimental results of anti-HBV activity in HepAD38 cells

| Examples No. | $EC_{50}$ (nM) |
|---|---|
| 1 | 24 |

TABLE 2

Experimental results of anti-HBV activity in HepG2.2.15 cells

| Examples No. | $EC_{50}$ (nM) |
|---|---|
| 1 | 17.4 |
| 2 | 10.7 |

1.2 In Vitro Cytotoxicity

A bottle of HepG2.2.15 cells (Wuhan Institute of Virology) in good exponential growth state was taken, washed once by adding 5 mL PBS, and then thereto was added 2 mL trypsin. The sample was digested in a cell culture incubator, and taken out from time to time and observed under a microscope. When the cells just fell off, 1 mL trypsin was discarded. The residual liquid was placed in a cell culture incubator at 37° C. and digested for 8-15 min. The cells were taken out and observed under a microscope (whether the cells were individually round and there was no adhesion between the cells). 5 mL MEM medium was added for cell resuspension. The cells were then subjected to cell counting with a cell counter, diluted with a complete medium, and adjusted to a cell density of $2*10^5$ cells/mL. Then the cells were seeded at 100 μL/well in a 96-well plate with a multi-channel pipette (the 96-well plate was coated with 50 μg/mL Collagen I solution in advance), and cultured in a constant temperature $CO_2$ incubator for 24 h. The cells were treated by drug administration, and fresh medium containing the compound was used to replace the spent medium every 3 days. To control wells was added a drug-free medium containing 0.5% DMSO, and a control well containing a common medium was set up. 6 days after the administration, CCK-8 was added at 10 μL/well. After 1 to 2 hours, the absorbance was detected with microplate reader at 450 nm, and the inhibition rate and the CC50 were calculated. The results are shown in Table 3.

TABLE 3

| Cells | $CC_{50}$(μM) | Example No. |
|---|---|---|
| HepG2.2.15 | >100 | 1 |

1.3 CYP450 Enzyme Inhibition Study

500 μL of a final incubation system contains 50 μL of human liver microsomes (protein concentration: 0.2 mg/mL, Corning), 1 μL of mixed CYP450 specific substrates (CYP1A2, CYP 2B6, CYP 2C9, CYP2C19, CYP 2D6, and CYP 3A4), 398 μL PBS buffer (pH7.4), 1 μL specific positive inhibitor (positive control group) or the test compound (formulated with acetonitrile), and 50 μL NADPH+$MgCl_2$. Duplicate incubation systems of 0.5 mL each were formulated for each CYP450 subtype. A total volume of 450 μL of a uniformly mixed solution of the substrate and the enzyme was formulated in each tube, and the solution and NADPH were pre-incubated at 37° C. for 5 minutes, respectively. Then 50 μL of the mixed solution of NADPH+$MgCl_2$ was added for reaction. 50 μL of the reaction solution was taken out at 30 minutes, and the reaction was terminated with 300 μL of ice acetonitrile containing an internal standard. In addition, two control groups of 500 μL each without NADPH were prepared in parallel as a negative control group.

Sample pre-treatment: To 50 μL of the incubated sample was added 300 μL of ice acetonitrile containing an internal standard, and then precipitated. After vortexing for 5 minutes, the sample was centrifugated (12000 rpm, 4° C.) for 10 minutes. 75 μL of the supernatant was pipetted, and 75 μL of ultrapure water was added thereto for dilution and mixed uniformly. 1 μL of the resulting solution was injected for analysis. The results are shown in Table 4.

TABLE 4

| Examples No. | Subtypes $IC_{50}$ (μM) | | | | | |
|---|---|---|---|---|---|---|
| | 3A4 | 2D6 | 2C19 | 2C9 | 2B6 | 1A2 |
| 1 | >200 | 54 | 20 | >200 | >200 | 49 |

1.4 Plasma Protein Binding Assay

Formulation of plasma sample: 495 μL of blank plasmas of the corresponding species (mouse, rat, dog, monkey, and human) were drawn respectively, and thereto was added 5 μL of the corresponding test compound solution or positive control to give plasma sample solutions having a plasma drug concentration of the compound of 1 μM, and 10 μM, respectively (formulated with acetonitrile).

The pre-treated dialysis membrane was placed in a high-throughput equilibrium dialysis device, and 100 μL of the plasma sample solution and PBS buffer solution were drawn and added respectively to both sides of the dialysis membrane (sample side and buffer side) (n=3). After the equilibration device was sealed with a film, it was incubated at 37° C. overnight (100 rpm). After dialysis equilibrium was reached, 50 μL samples were drawn from the sample side and the buffer side, respectively, and the reaction was terminated by adding ice acetonitrile containing an internal standard.

Sample pre-treatment: To 50 μL of the plasma-side sample was added 450 μL of ice acetonitrile containing an internal standard, and then precipitated. After vortexing for 5 minutes, the sample was centrifugated (12000 rpm, 4° C.) for 10 minutes. 75 μL of the supernatant was pipetted, and 75 μL of ultrapure water was added thereto for dilution and mixed uniformly. 1 μL of the resulting solution was injected for analysis. To 50 μL of the PBS-side sample was added 250 μL of ice acetonitrile with an internal standard, and precipitated. After vortexing for 5 min, the sample was centrifugated (12000 rpm, 4° C.) for 10 min. 75 μL of the supernatant was pipetted, and 75 μL of ultrapure water was added thereto for dilution and mixed uniformly. 2 μL of the resulting solution was injected for analysis. The results are shown in Table 5.

TABLE 5

| Examples No. | Concentration | Binding rate (%) | | | | |
|---|---|---|---|---|---|---|
| | | Human | Rat | Mouse | Dog | Monkey |
| 1 | 1 μM | 97.3 | 95.0 | 85.4 | 94.0 | 90.2 |
| | 10 μM | 97.3 | 95.3 | 85.5 | 93.9 | 90.5 |

Experimental Example 2: Stability of Liver Microsomes In Vitro

300 μL of a final incubation system contains 30 μL of liver microsomes (protein concentration: 0.15 mg/mL, Corning), 30 μL NADPH+$MgCl_2$, 3 μL substrate (formulated with acetonitrile), and 237 μL PBS buffer. Duplicate incubation systems of 0.3 mL each were formulated for each species. A total volume of 270 μL of a uniformly mixed solution of the substrate and the enzyme was formulated in each tube, the solution and NADPH were pre-incubated at 37° C. for 5 minutes, respectively. Then 30 μL of the mixed solution of NADPH+$MgCl_2$ was added for reaction. 50 μL of the reaction solution was taken out at 0, 10, 30, and 60 mins, and the reaction was terminated with 300 μL of ice acetonitrile containing an internal standard.

Sample pre-treatment: To 50 μL of the incubated sample was added 300 μL of ice acetonitrile containing diazepam as an internal standard and then precipitated. After vortexing for 5 minutes, the sample was centrifugated (12000 rpm, 4° C.) for 10 minutes. 75 μL of the supernatant was pipetted into a 96-well plate, and then diluted with 75 μL ultrapure water and mixed uniformly. 0.5 μL of the resulting solution was injected and analyzed by LC-MS/MS. The results are shown in Table 6.

TABLE 6

Stability of liver microsomes in vitro

| Examples No. | Remaining (%) of human liver microsomes at 60 min | Remaining (%) of rat liver microsomes at 60 min | Remaining (%) of mouse liver microsomes at 60 min |
|---|---|---|---|
| 1 | 99 | 99 | 96 |
| 2 | 100 | 99 | 100 |

Experimental Example 3: In Vivo Animal Efficacy 3.1 Antiviral Effect Evaluation in AAV Mouse Model 6-8 week old male C57BL/6 mice (Shanghai Lingchang Biotechnology Co., Ltd.) were injected with rAAV8-1.3HBV virus (Beijing FivePlus Gene Technology Ltd., adr subtype) at tail vein at a dose of $1×10^{11}$ vg. Blood was collected from the orbits of the mice on week 2 and 4 after the virus injection. The serum was separated, and the expression levels of HBeAg and HBsAg in the serum and the HBV DNA copy number were detected to evaluate whether the model was successfully established. According to the results of quantitative detection of serological HBeAg, HBsAg and HBV DNA, the mice having HBV DNA expression level greater than $1×10^4$ IU/mL, HBeAg expression level greater than $1×10^3$ NCU/mL and HBsAg expression level greater than $1×10^3$ ng/mL were selected. The mice were grouped into a blank control group, a vehicle control group, and a test substance group. The mice in each group were continuously administered intragastrically once daily for 3 weeks and then the administration was suspended for 1 week. During the experiment, blood was collected from the orbits every other week, serum was separated, and the DNA content was detected by fluorescent quantitative PCR method. The results are shown in Tables 7 and 8.

TABLE 7

Reduction levels (log10) of HBV DNA in serum (dose: 10 mpk)

| Examples No. | Day 7 | Day 14 | Day 21 | Day 28 |
|---|---|---|---|---|
| 1 | 2.67 | 3.80 | 4.30 | 3.50 |

TABLE 8

Reduction levels (log10) of HBV DNA in serum (dose: 1 mpk)

| Examples No. | Day 7 | Day 14 | Day 21 | Day 28 |
|---|---|---|---|---|
| 1 | 2.49 | 3.41 | 3.65 | 3.25 |

3.2 Experimental Method of pAAV/HBV Model 6-8 week old male C57BL/6 mice (Shanghai Lingchang Biotechnology Co., Ltd.) were used, and each mouse was injected with purified recombinant plasmid pAAV/HBV1.2 (10 g) dissolved in PBS equivalent to a volume of about 10% of its body weight through the tail vein within 3-8 s. Blood was collected from the orbits of the mice at 3 days after the plasmid injection to detect serum HBV DNA. The model mice having uniform serum DNA were selected and divided into: a model control group, a vehicle control group, and a test substance group. Mice in each group were continuously administered intragastrically once daily for 10 days at a dose of 3 mg/kg. The mouse serum was taken on day 0, 4, 7, and 10 after the administration, and the mice were sacrificed on day 10 to take liver tissue samples. The HBV DNA copy numbers in serum and liver of the mice were detected by fluorescent quantitative PCR method. The results are shown in Table 9.

TABLE 9

Reduction levels (log10) of HBV DNA in serum (dose: 3 mpk)

| Examples No. | Day 4 | Day 7 | Day 10 |
|---|---|---|---|
| 1 | 2.95 | 4.13 | 2.71 |
| 2 | 2.92 | 4.09 | 2.42 |

Experimental Example 4: In Vivo Pharmacokinetics

In Vivo Pharmacokinetics (PK) Study in Rats

SD rats (Shanghai Xipuer-Bikai Laboratory Animal Co., Ltd.), weighing 180~220 g, were randomly divided into groups of three mice each after 3 to 5 days' acclimatization, and a series of the compounds were administered intragastrically to each group at a dose of 20 mg/kg.

The test animals (SD rats) were fasted for 12 hours before administration and fed 4 hours after the administration. They were free to access water before and after the experiment.

After the administration, about 0.2 mL of blood from the orbits was collected at 0 min, 15 min, 30 min, 1 h, 2 h, 4 h, 6 h, 8 h, 10 h, 24 h, 30 h, and 48 h. Within 30 minutes after anticoagulation with EDTA-K2, the plasma was separated by centrifugation at 4° C. and 4000 rpm for 10 minutes. Immediately after collecting all plasma, it was stored at −20° C. for testing.

50 μL of the plasma sample to be tested and standard curve sample were pipetted, and then thereto was added 500 μL of an acetonitrile solution containing an internal standard (diazepam 20 mg/mL). The resulting mixture was oscillated and mixed uniformly for 5 min, and then centrifugated at 12000 rpm for 10 min. 75p L supernatant was pipetted, and 75 μL ultrapure water was added thereto for dilution, and mixed evenly. 1 μL of the resulting solution was pipetted for LC/MS/MS determination. The results are shown in Table 10.

TABLEs 10

| | Example No. 1 | |
|---|---|---|
| Mode of administration and dosage | IV 5 mg/kg | PO 10 mg/kg |
| $T_{1/2}$ (h) | 52.8 | 45.6 |
| Vz (mL/kg) | 2.58 | NA |
| Cl (mL/h/kg) | 0.03 | NA |

TABLEs 10-continued

| | Example No. 1 | |
|---|---|---|
| Mode of administration and dosage | IV 5 mg/kg | PO 10 mg/kg |
| $C_{max}$ (ng/mL) | 3512 | 4111 |
| $AUC_{(0-48\ h)}$ (ng*h/mL) | 126939 | 254490 |
| $AUC_{(0-\infty)}$ (ng*h/mL) | 147701 | 283784 |
| F (%) | NA | 100% |

NA means not available.

What is claimed:

1. A compound of Formula I or II, a stereoisomer, a tautomer, a solvate, a hydrate, or a pharmaceutically acceptable salt thereof,

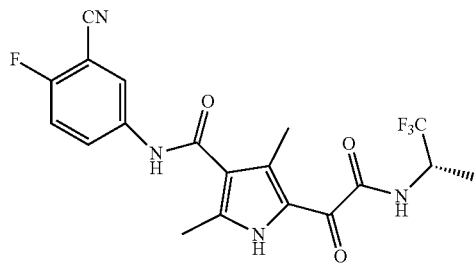

I

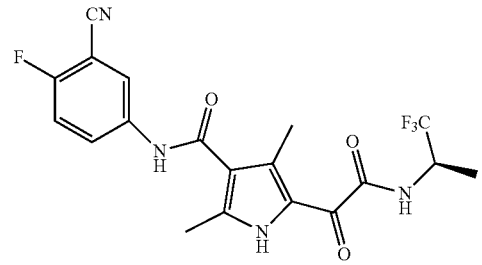

II

2. A pharmaceutical composition comprising a compound of Formula I or II, a stereoisomer, a tautomer, a solvate, a hydrate, or a pharmaceutically acceptable salt thereof according to claim 1.

3. A method of treating a disease caused by hepatitis B virus infection, comprising administering to a subject in need thereof a therapeutically effective amount of a compound of Formula I or II, a stereoisomer, a tautomer, a solvate, a hydrate, or a pharmaceutically acceptable salt thereof according to claim 1, or a pharmaceutical composition thereof.

4. The pharmaceutical composition according to claim 2, further comprising a pharmaceutically acceptable excipient.

* * * * *